United States Patent [19]

Kawai et al.

[11] Patent Number: 5,684,211
[45] Date of Patent: Nov. 4, 1997

[54] METHOD OF PURIFYING FLUOROMETHYL-1,1,1,3,3,3-HEXAFLUOROISOPROPYL ETHER

[75] Inventors: Toshikazu Kawai; Takaaki Yoshimura; Manami Kumakura; Mineo Watanabe, all of Kawagoe, Japan

[73] Assignee: Central Glass Company, Limited, Yamaguchi, Japan

[21] Appl. No.: 553,662

[22] PCT Filed: Mar. 23, 1995

[86] PCT No.: PCT/JP95/00537

§ 371 Date: Nov. 16, 1995

§ 102(e) Date: Nov. 16, 1995

[87] PCT Pub. No.: WO95/26949

PCT Pub. Date: Dec. 10, 1995

[30] Foreign Application Priority Data

Mar. 31, 1994 [JP] Japan ................................ 6-063465

[51] Int. Cl.$^6$ ........................................................ C07C 41/00
[52] U.S. Cl. ........................................ 568/682; 568/683
[58] Field of Search ........................................ 568/682, 683

[56] References Cited

U.S. PATENT DOCUMENTS 4,250,334  2/1981  Coon et al. .
4,328,376  5/1982  Berger et al. .

*Primary Examiner*—José G. Dees
*Assistant Examiner*—Karl J. Puttlitz, Jr.
*Attorney, Agent, or Firm*—Keck, Mahin & Cate

[57] ABSTRACT

The present invention provides a method of purifying fluoromethyl-1,1,1,3,3,3-hexafluoroisopropyl ether by adding a compound selected from hydroxides of, hydrogenphosphates of, phosphates of, hydrogencarbonates of, borates of or sulfites of alkali metals, or alkali metal salts of acetic acid or of phthalic acid, or boric acid to fluoromethyl-1,1,1,3,3,3-hexafluoroisopropyl ether, add then by distillation. It is possible to effectively suppress the decomposition, at the time of distillation, of fluoromethyl-1,1,1,3,3,3-hexafluoroisopropyl ether that is used as a pharmaceutical and particularly as an inhalation anesthetic and thus to obtain fluoromethyl-1,1,1,3,3,3-hexafluoroisopropyl ether of high purity.

6 Claims, No Drawings

METHOD OF PURIFYING FLUOROMETHYL-1,1,1,3,3,3-HEXAFLUOROISOPROPYL ETHER

TECHNOLOGICAL FIELD

The present invention relates to a method of purifying fluoromethyl-1,1,1,3,3,3-hexafluoroisopropyl ether, which is widely used as a pharmaceutical and particularly as an inhalation anesthetic. In more detail, it relates to a method of suppressing decomposition of fluoromethyl-1,1,1,3,3,3-hexafluoroisopropyl ether at the time of distillation and thus obtaining fluoromethyl-1,1,1,3,3,3-hexafluoroisopropyl ether of high purity.

BACKGROUND TECHNOLOGY

Hitherto, fluoromethyl-1,1,1,3,3,3-hexafluoroisopropyl ether has been widely used as a safe inhalation anesthetic.

This fluoromethyl-1,1,1,3,3,3-hexafluoroisopropyl ether can be obtained, for example, by reacting together fluoromethyl-1,1,1,3,3,3-hexafluoroisopropyl alcohol, formaldehyde, and hydrogen fluoride. The thus produced crude fluoromethyl-1,1,1,3,3,3-hexafluoroisopropyl ether contains various by-products. A means is selected to remove these by-products by passing the reaction product through usual treatment steps, that is, steps such as washing with acid, washing with alkali, washing with water, distillation, and the like.

However, in the distillation step of this fluoromethyl-1,1,1,3,3,3-hexafluoroisopropyl ether, it was found that crude fluoromethyl-1,1,1,3,3,3-hexafluoroisopropyl ether decomposes or disproportionates and thus can not be distilled and that impurities thus increase. In other words, it was found that defluorohydrogenation of fluoromethyl-1,1,1,3,3,3-hexafluoroisopropyl ether occurs during distillation and that fluoromethyl-1,1,3,3,3-pentafluoroisopropenyl ether is gradually formed as a new impurity. This fluoromethyl-1,1,3,3,3-pentafluoroisopropenyl ether which is a decomposition product of fluoromethyl-1,1,1,3,3,3-hexafluoroisopropyl ether is a volatile analogous compound of fluoromethyl-1,1,1,3,3,3-hexafluoroisopropyl ether, and can not be separated because their boiling points are nearly the same. It is needless to say that the contamination of the product thereby is extremely unfavorable in use as an inhalation anesthetic, and thus an immediate solution has been desired.

DISCLOSURE OF THE INVENTION

In view of such problem in the past, the present inventors have eagerly examined a method of distilling fluoromethyl-1,1,1,3,3,3-hexafluoroisopropyl ether, in which method the decomposition of fluoromethyl-1,1,1,3,3,3-hexafluoroisopropyl ether is suppressed and fluoromethyl-1,1,3,3,3-pentafluoroisopropenyl ether is not formed. As a result, we have found that the decomposition of fluoromethyl-1,1,1,3,3,3-hexafluoroisopropyl ether can be suppressed and thus fluoromethyl-1,1,1,3,3,3-hexafluoroisopropyl ether of high purity essentially not containing fluoromethyl-1,1,3,3,3-pentafluoroisopropenyl ether can be obtained by adding a compound selected from hydroxides of, hydrogenphosphates of, phosphates of, hydrogencarbonates of, borates of or sulfites of alkali metals, or alkali metal salts of acetic acid or of phthalic acid, or boric acid, in the form of solid as it is or of aqueous solution, to fluoromethyl-1,1,1,3,3,3-hexafluoroisopropyl ether, and then by conducting distillation. Thus, we have achieved the present invention.

In other words, the present invention provides a method of purifying fluoromethyl-1,1,1,3,3,3-hexafluoroisopropyl ether, characterized in that a compound selected from hydroxides of, hydrogenphosphates of, phosphates of, hydrogencarbonates of, borates of or sulfites of alkali metals, or alkali metal salts of acetic acid or of phthalic acid, or boric acid is added to fluoromethyl-1,1,1,3,3,3-hexafluoroisopropyl ether, followed by distillation.

Additives for suppressing decomposition of fluoromethyl-1,1,1,3,3,3-hexafluoroisopropyl ether used in the present invention are hydroxides of, hydrogenphosphates of, phosphates of, hydrogencarbonates of, borates of or sulfites of alkali metals, or alkali metal salts of acetic acid or of phthalic acid, or boric acid. Hydroxides of alkali metals are NaOH, KOH, and the like. Hydrogenphosphates of alkali metals are hydrogenphosphates of or dihydrogenphosphates of alkali metals. To be concrete, they are $Na_2HPO_4$, $NaH_2PO_4$, $K_2HPO_4$, $KH_2PO_4$, and the like. Phosphates of alkali metals represent metaphosphates of and polyphosphates of alkali metals as well as orthophosphates of alkali metals. To be concrete, they are $Na_3PO_4$, $K_3PO_4$, $(NaPO_3)_3$, $(NaPO_3)_4$, $(KPO_3)_3$, $(KPO_3)_4$, and the like. Hydrogencarbonates of alkali metals are $NaHCO_3$, $KHCO_3$, and the like. Borates of alkali metals represent diborates of, metaborates of, tetraborates of, pentaborates of, hexaborates of, and octaborates of alkali metals, and the like. To be concrete, they are $NaBO_2$, $Na_2B_4O_7$, $NaB_5O_8$, $Na_2B_6O_{10}$, $Na_2B_8O_{18}$, $Na_4B_2O_5$, $KBO_2$, $K_2B_4O_7$, $KB_5O_8$, $K_2B_6O_{10}$, $K_2B_8O_{18}$, and the like. Sulfites of alkali metals are $Na_2SO_3$, $K_2SO_3$, and the like. Furthermore, alkali metal salts of acetic acid are $CH_3COONa$, $CH_3COOK$, and the like. Alkali metal salts of phthalic acid are alkali metal salts of o-phthalic acid, of m-phthalic acid or of p-phthalic acid. To be concrete, they are o-$C_6H_4(COOK)(COOH)$, m-$C_6H_4(COOK)(COOH)$, p-$C_6H_4(COOK)(COOH)$, o-$C_6H_4(COONa)(COOH)$, m-$C_6H_4(COONa)(COOH)$, p-$C_6H_4(COONa)(COOH)$, and the like. Of the above additives, preferable ones which have a great advantage particularly in suppressing decomposition of fluoromethyl-1,1,1,3,3,3-hexafluoroisopropyl ether are $NaHCO_3$, $Na_2B_4O_7$, $H_3BO_4$, $C_6H_4(COOK)(COOH)$, $Na_2SO_3$, $Na_2HPO_4$, $CH_3COONa$, $Na_3PO_4$, and the like. Of these, $H_3BO_4$, $C_6H_4(COOK)(COOH)$, $Na_2HPO_4$, $CH_3COONa$, and the like, which show a more superior advantage, are more preferable additives.

In the present invention, distillation of fluoromethyl-1,1,1,3,3,3-hexafluoroisopropyl ether is conducted by adding the above decomposition suppressive agent(s). These decomposition suppressive agents can be added in the form of solid as it is or of aqueous solution.

In case that it is added in the form of solid as it is, the above-mentioned decomposition suppressive agent(s) of the present invention may be used in the form of anhydride or of hydrate. Furthermore, their forms upon addition are not particularly limited, and thus any forms may be used, such as powdery, granular, flaky and pelletlike forms. However, it is more effective to make their form as fine as possible because the surface area increases and because they easily diffuse. Therefore, more preferable one is powdery form.

Furthermore, in case that the decomposition suppressive agent is added in the form of solid as it is, the amount of addition is not particularly limited. It is preferably from 0.01 wt % to 10 wt %, based on fluoromethyl-1,1,1,3,3,3-hexafluoroisopropyl ether to be treated, more preferably from 0.05 wt % to 5 wt %, and still more preferably from 0.1 wt % to 1 wt %. If it is less than this range, a sufficient decomposition suppressive advantage may not be obtained. This is not preferable. Furthermore, even if it is more than this range, the decomposition suppressive advantage does not particularly change, and only economical disadvantage is caused. Therefore, this is not preferable.

However, as is mentioned above, when the decomposition suppressive agent is added in the form of solid as it is, for example, in case that it is in a fine form such as powdery form, the inside of the system becomes slurry. Therefore, this is not preferable. Furthermore, in case that it is in a large form such as pelletlike form, it does not become slurry, but a sufficient decomposition suppressive advantage may not be obtained. Therefore, this is still not preferable. Therefore, as is described hereinafter, it is more preferable that the decomposition suppressive agent is added in the form of aqueous solution.

In case that the decomposition suppressive agent is added in the form of aqueous solution, its concentration is not particularly limited. However, it is appropriately from 0.01 wt % to saturated solution, more preferably from 0.1 wt % to 10 wt %, and still more preferably from 1 wt % to 5 wt %. In case that the concentration is lower than this range, a sufficient decomposition suppressive advantage may not be obtained, and it may become necessary to add a large amount of aqueous solution for obtaining a sufficient decomposition suppressive advantage. Therefore, this is not preferable. Furthermore, as distillation of fluoromethyl-1,1,1,3,3,3-hexafluoroisopropyl ether proceeds, water in the system is also distilled out. Therefore, if the aqueous solution of too high concentration is used, it is concentrated. With this, solid matter precipitates, and the inside of the system becomes slurry. Therefore, this is not preferable.

Furthermore, in case that the decomposition suppressive agent is added in the form of aqueous solution, the amount of addition is not particularly limited, but a suitable amount of addition may be selected according to the concentration of the aqueous solution. For example, in case that the concentration of the aqueous solution is 1 wt %, it is appropriately from 1 wt % to 200 wt %, based on fluoromethyl-1,1,1,3,3,3-hexafluoroisopropyl ether to be treated, more preferably from 3 wt % to 100 wt %, and still more preferably from 5 wt % to 50 wt %. If it is less than this range, a sufficient decomposition suppressive advantage may not be obtained. Therefore, this is not preferable. Furthermore, even if it is more than this range, the decomposition suppressive advantage does not particularly change, and only economical disadvantage is caused. Furthermore, this leads to the increase of the distillate volume. Therefore, this is not preferable.

THE BEST MODE TO CARRY OUT THE INVENTION

Hereinafter, the present invention will be described in more detail with reference to Examples.

EXAMPLE 1

A 30 ml three-neck flask provided with a condenser tube was charged with 20.0 g of fluoromethyl-1,1,1,3,3,3-hexafluoroisopropyl ether and 1.4 g (7 wt % based on fluoromethyl-1,1,1,3,3,3-hexafluoroisopropyl ether) of an aqueous solution of an additive of 1 wt %, followed by heating in oil bath. The temperature of the oil bath was set at 110° C., and heating under reflux was conducted. Behavior of fluoromethyl-1,1,3,3,3-pentafluoroisopropenyl ether was identified by conducting analysis by gas chromatography, 4 hours and 8 hours after. The results are shown in Table 1.

TABLE 1

| Additives | Fluoromethyl-1,1,3,3,3-pentafluoroisopropenyl ether (ppm) | | |
|---|---|---|---|
| | Raw Material | 4 hours after | 8 hours after |
| $NaHCO_3$ | 39 | 54 | 82 |
| $Na_2B_4O_7 \cdot 10H_2O$ | 39 | 41 | 44 |
| $H_3BO_4$ | 39 | 38 | 37 |
| $C_6H_4(COOK)(COOH)$ | 39 | 37 | 36 |
| $Na_2SO_3$ | 39 | 43 | 48 |
| $Na_2HPO4$ | 39 | 37 | 30 |
| $CH_3COONa$ | 39 | 35 | 37 |
| $Na_2PO_4 \cdot 12H_2O$ | 39 | 49 | 51 |

From Table 1, it is understood that, in any case, decomposition of fluoromethyl-1,1,1,3,3,3-hexafluoroisopropyl ether is well suppressed, and thus that formation of fluoromethyl-1,1,3,3,3-pentafluoroisopropenyl ether is effectively suppressed. In particular, when $H_3BO_4$, $C_6H_4(COOK)(COOH)$, $Na_2HPO_4$ or $CH_3COONa$ is used, the content of fluoromethyl-1,1,3,3,3-pentafluoroisopropenyl ether decreases, and decomposition of fluoromethyl-1,1,1,3,3,3-hexafluoroisopropyl ether is completely suppressed. Therefore, these compounds are particularly superior decomposition suppressive agents.

EXAMPLE 2

Distillation of fluoromethyl-1,1,1,3,3,3-hexafluoroisopropyl ether was conducted, using a distillation tower which has a tower height of 1 m and an inside diameter of 12 mm and is packed with coiled glass Raschig rings of 3 mm φ×5 mm. It was charged with fluoromethyl-1,1,1,3,3,3-hexafluoroisopropyl ether and 7 wt %, based on this, of $Na_2HPO_4$ aqueous solution, followed by distillation. At first, total reflux was conducted. One hour after, the initial distillate was removed under a reflux ratio of 20. At the time when the purity of fluoromethyl-1,1,1,3,3,3-hexafluoroisopropyl ether became at least 99.0%, it was changed to the main distillate, and the main distillate was removed under a reflux ratio of 10. The distillation was terminated when the distillate of fluoromethyl-1,1,1,3,3,3-hexafluoroisopropyl ether ended at an oil bath temperature of 105° C. or when the purity of fluoromethyl-1,1,1,3,3,3-hexafluoroisopropyl ether of the distillate became less than 99.0%. The results are shown in Table 2. Furthermore, the analysis was conducted by gas chromatography. (The following is a blank space.)

TABLE 2

| No. | | | Weight (g) | Fluoromethyl-1,1,3,3,3-pentafluoroisopropenyl ether (%) | Fluoromethyl-1,1,1,3,3,3-hexafluoroisopropyl ether (%) |
|---|---|---|---|---|---|
| 1 | Charge | Fluoromethyl-1,1,1,3,3,3-hexafluoroisopropyl ether | 250 | 0.003 | 92.129 |
| | | 2 wt %-$Na_2HPO4$ | 17.5 | — | — |
| | Distillate | Initial Distillate | 18.9 | 0.030 | 99.774 |
| | | Main Distillate (Yield: 71.4%) | 178.5 | Not detected | 99.995 |
| | | Residue | 39.7 | Not detected | 51.380 |
| 2 | Charge | Fluoromethyl-1,1,1,3,3,3- | 500 | 0.001 | 89.299 |

TABLE 2-continued

| No. | | Weight (g) | Fluoromethyl-1,1,3,3,3-pentafluoroisopropenyl ether (%) | Fluoromethyl-1,1,1,3,3,3-hexafluoroisopropyl ether (%) |
|---|---|---|---|---|
| | hexafluoroisopropyl ether 1 wt %-Na$_2$HPO4 | 35.0 | — | — |
| Distillate | Initial Distillate | 44.5 | 0.008 | 99.647 |
| | Main Distillate (Yield: 71.7%) | 358.4 | Not detected | 99.928 |
| | Residue | 84.0 | Not detected | 37.226 |

As is seen from Table 2, fluoromethyl-1,1,3,3,3-pentafluoroisopropenyl ether that had been originally contained in fluoromethyl-1,1,1,3,3,3-hexafluoroisopropyl ether which is a charged raw material, was removed by the initial distillate by conducting distillation with the addition of the decomposition suppressive agent. Furthermore, the main distillate is never contaminated with fluoromethyl-1,1,3,3,3-pentafluoroisopropenyl ether caused by the decomposition of fluoromethyl-1,1,1,3,3,3-hexafluoroisopropyl ether. Still furthermore, the purity of the main distillate is at least 99.9% and thus high, and the yield is at least 70%. Therefore, it is understood that the distillation is well conducted.

INDUSTRIAL APPLICABILITY

According to the method of the present invention, it is possible to effectively suppress the decomposition, at the time of distillation, of fluoromethyl-1,1,1,3,3,3-hexafluoroisopropyl ether that is used as a pharmaceutical and particularly as an inhalation anesthetic and thus to obtain fluoromethyl-1,1,1,3,3,3-hexafluoroisopropyl ether of high purity.

We claim:

1. A method of purifying fluoromethyl-1,1,1,3,3,3-hexafluoroisopropyl ether by distillation, characterized in that the distillation is conducted in the presence of a compound selected from the group consisting of hydroxides of alkali metals, hydrogenphosphates of alkali metals, phosphates of alkali metals, hydrogencarbonates of alkali metals, borates of alkali metals, sulfites of alkali metals, alkali metal salts of acetic acid, alkali metal salts of phthalic acid and boric acid.

2. A method of purifying fluoromethyl-1,1,1,3,3,3-hexafluoroisopropyl ether according to claim 1, wherein said compound is NaHCO$_3$, Na$_2$B$_4$O$_7$, H$_3$BO$_4$, C$_6$H$_4$(COOK)(COOH), Na$_2$SO$_3$, Na$_2$HPO$_4$, CH$_3$COONa, or Na$_3$PO$_4$.

3. A method of purifying fluoromethyl-1,1,1,3,3,3-hexafluoroisopropyl ether according to claim 1, wherein said compound is H$_3$BO$_4$, C$_6$H$_4$(COOK)(COOH), Na$_2$HPO$_4$, or CH$_3$COONa.

4. A method of purifying fluoromethyl-1,1,1,3,3,3-hexafluoroisopropyl ether according to claim 1, wherein said compound is added in the form of aqueous solution.

5. A method of purifying fluoromethyl-1,1,1,3,3,3-hexafluoroisopropyl ether according to claim 2, wherein said compound is added in the form of aqueous solution.

6. A method of purifying fluoromethyl-1,1,1,3,3,3-hexafluoroisopropyl ether according to claim 3, wherein said compound is added in the form of aqueous solution.

* * * * *